United States Patent [19]

Mirsch, II et al.

[11] Patent Number: 5,728,152
[45] Date of Patent: Mar. 17, 1998

[54] BIORESORBABLE HEART VALVE SUPPORT

[75] Inventors: M. William Mirsch, II, Roseville; Katherine S. Tweden, Mahtomedi; Todd D. Campbell, Bear Lake; Bruce D. Ward, Woodbury, all of Minn.

[73] Assignee: St. Jude Medical, Inc., St. Paul, Minn.

[21] Appl. No.: 484,189

[22] Filed: Jun. 7, 1995

[51] Int. Cl.$^6$ ........................................... A61F 2/24
[52] U.S. Cl. ........................... 623/2; 623/1; 623/900
[58] Field of Search ................................ 623/1, 2, 900

[56] References Cited

U.S. PATENT DOCUMENTS

| | | | |
|---|---|---|---|
| 4,680,031 | 7/1987 | Alonso . | |
| 4,753,652 | 6/1988 | Langer et al. | 623/1 |
| 4,816,029 | 3/1989 | Penny, III et al. | 623/2 |
| 5,080,670 | 1/1992 | Imamura et al. | 623/2 |
| 5,085,629 | 2/1992 | Goldberg et al. . | |
| 5,133,755 | 7/1992 | Brekke . | |
| 5,258,021 | 11/1993 | Duran | 623/2 |
| 5,306,286 | 4/1994 | Stack et al. . | |
| 5,376,112 | 12/1994 | Duran . | |
| 5,412,068 | 5/1995 | Tang et al. . | |
| 5,489,297 | 2/1996 | Duran | 623/2 |

FOREIGN PATENT DOCUMENTS 2 206 395   1/1989   United Kingdom .

OTHER PUBLICATIONS

Hiratzka et al., Arch. Surg., 114:698–702, 1979.
Jamshidi et al., Trans. Am. Soc. Artif. Intern. Organs, 34:755–760, 1988.
Hubbell et al., C&EN, pp. 42–54, 1995.
Beck et al., FASEB, 4:148–160, 1990.
Ruoslahti et al., Science, 238:491–497, 1987.
Hubbell et al., Bio/Technology, 9:586–572, 1991.
Humphries et al., J. of Cell Biol., 103:2637–2647, 1986.
Graf et al., Cell, 48:989–996, 1987.
R. Hynes, Cell, 69:11–25, 1992.
Loike et al., Proc. Natl. Acad. Sci. USA, 88:1044–1048, 1991.
Van Der Lei et al., Int. Angiol., 10:202–208, 1991.
Murray et al., Cancer Drug Delivery, 1:119–123, 1984.
David et al., J. Heart Valve Dis., 1:244–248, 1992.
R. Hopkins, Cardiac Reconstructions with Allograft Valves, Springer-Verlag (1989), pp. 97–122.

*Primary Examiner*—John G. Weiss
*Assistant Examiner*—Francis K. Cuddihy
*Attorney, Agent, or Firm*—Hallie A. Finucane; Fish & Richardson P.C., P.A.

[57] ABSTRACT

This invention relates to bioprosthetic heart valve stents that are fashioned of bioresorbable materials. Such stents may be configured as sheaths or frames contoured to the shape of a valvular graft. The stents are eventually resorbed by the patient, leaving a functional "stentless" valve with improved hemodynamic characteristics compared to stented valve implants.

12 Claims, 3 Drawing Sheets

BIORESORBABLE HEART VALVE SUPPORT

FIELD OF THE INVENTION

This invention relates to bioprosthetic heart valves combining the advantages of stented and stentless valves. More particularly, the invention relates to biocompatible heart valve stents that are resorbed by the patient following implantation.

BACKGROUND OF THE INVENTION

Prosthetic heart valves may be used to replace diseased natural heart valves in human patients. Mechanical heart valves typically have a rigid orifice ring and rigid hinged leaflets coated with a blood compatible substance such as pyrolytic carbon. Other configurations, such as ball-and-cage assemblies, have also been used for such mechanical valves.

In contrast to mechanical heart valves, bioprosthetic heart valves comprise valve leaflets formed of biological material. Many bioprosthetic valves include a support structure, or stent, for supporting the leaflets and maintaining the anatomical structure of the valve. Stented bioprosthetic valves generally are prepared in one of two ways. In a first method of preparation, a complete valve is obtained from either a deceased human or from a slaughtered pig or other mammal. Human valves or valve components implanted into a human patient are referred to herein as a "homografts," while the corresponding animal valves or valve components are termed "xenografts." In the case of homografts, the retrieved valve typically is treated with antibiotics and then cryopreserved in a solution of nutrient medium (e.g., RPMI), fetal calf serum and 10% DMSO. In the case of xenografts, the retrieved valve is trimmed to remove the aortic root, and the valve is chemically cross-linked, typically in a glutaraldehyde solution. The cross-linked valve is then attached to a stent. The stent provides structural support to the valve and, with a sewing cuff, facilitates attachment of the valve to the patient by suturing. In a second method of preparation, individual valve leaflets are removed from a donor valve or are fashioned from other sources of biological material, e.g., bovine pericardium. The individual leaflets are then assembled by suturing the valve leaflets both to each other and to the stent. When bovine pericardium is used, the valve (trileaflet or bileaflet) is fashioned from one piece of pericardium. The material is then draped on the stent to form the "cusps."

One of the major functions of stents is to serve as a framework for attachment of the valve and for suturing the valve into place in the human patient. Toward that end, stents are frequently covered with a sewable fabric, and have a cloth sewing or suture cuff, typically an annular sewing ring, attached to them. The annular sewing ring serves as an anchor for the sutures by which the valve is attached to the patient. Various stent designs have been implemented in a continuing effort to render valve implantation simpler and more efficient. Inevitably, however, a stent limits interactions with aortic wall dynamics and tends to inhibit natural valve movement. This results in post-operative transvalvular gradients with resultant additional work burden on the heart. In addition, a stent causes a reduction in size of the bioprosthetic valve that can be placed in a particular location, since the stent and sewing cuff occupy space that otherwise would be available for blood flow.

Stentless valves have demonstrated better hemodynamic function than stented valves. This is because stentless valves are sewn directly into the host tissues, without the need for extraneous structure such as a sewing cuff. Such extraneous structures inevitably compromise hemodynamics. Stentless valves closely resemble native valves in their appearance and function, and rely upon the patient's tissues to supply the structural support normally provided by a stent. The main disadvantage to stentless valves has been in their difficulty of implantation. Stentless valves require both inflow and outflow suturing, and physicians qualified to implant stented valves can lack the surgical training and experience required for implantation of stentless valves.

Some bioprosthetic valve manufacturers have attempted to develop methods and materials to ease the implantation of stentless valves, including holders, different suturing techniques or suturing aids. None of these approaches has significantly shortened implant times without adversely affecting valve performance.

Stents for bioprosthetic heart valves have been formed from a variety of non-resorbable materials including metals and polymers. With non-resorbable materials, the long-term fatigue characteristics of the material are of critical importance. Unusually short or uneven wear of a stent material may necessitate early and undesirable replacement of the valve. The selected material must also be biocompatible and have the desired stress/strain characteristics.

Various biodegradable materials have been suggested or proposed for use with vascular or non-vascular implants. For example, Goldberg et al., U.S. Pat. No. 5,085,629 discloses a biodegradable infusion stent for use in treating ureteral obstructions. Stack et al., U.S. Pat. No. 5,306,286 discloses an absorbable stent for placement within a blood vessel during coronary angioplasty. Duran, U.S. Pat. No. 5,376,112 discloses an annuloplasty ring to be implanted into the heart to function together with the native heart valve. Duran suggests (Col. 6, lines 6–8) without further elaboration that the annuloplasty ring could be fashioned of resorbable materials.

The prior art stents are designed primarily to maintain a fluid flow patency for a selected period of time. These stents are not designed to support a secondarily functional tissue such as a valve apparatus. Thus, the prior art does not teach or suggest that heart valve stents, with their particular configuration and stress/strain requirements, could be fashioned of bioresorbable materials.

SUMMARY OF THE INVENTION

The invention relates to a bioprosthetic heart valve comprising a valvular tissue graft secured to a biocompatible, resorbable heart valve stent. The stent facilitates surgical joining of the bioprosthetic heart valve with valve-receiving cardiac tissue of a heart patient. Importantly, the stent is operably resorbed by the patient following substantially complete healing of said heart valve with said valve-receiving cardiac tissue. That is, the material of the stent is broken down and resorbed or metabolized by the patient's body to the extent that the stent no longer contributes substantially to the structure or function of the implanted bioprosthesis.

The valvular tissue graft of the bioprosthetic heart valve may be adapted to function at the aortic, mitral, tricuspid or pulmonic valve positions of the heart. Moreover, the stent of the present invention may comprise a sheath-type or frame-type stent structure of generally annular configuration, with either structure being contoured to the shape of the valvular tissue graft.

The sheath or frame may comprise a biocompatible, resorbable polymer, including without limitation dextran, hydroxyethyl starch, gelatin, derivatives of gelatin, polyvinylpyrolidone, polyvinyl alcohol, poly[N-(2-hydroxypropyl)methacrylamide], polyglycols, polyesters, poly (orthoesters), poly (ester-amides) and polyanhydrides. The polyesters may include without limitation poly (hydroxy acids) and copolymers thereof, poly ([epsilon]-caprolactone), poly (dimethyl glycolic acid) and poly-(hydroxy butyrate). Most preferably the-polymer comprises D,L-polylactic acid, L-polylactic acid, or glycolic acid, or copolymers of D,L-polylactic acid, L-polylactic acid, and glycolic acid.

A sheath-type or frame-type stent of the present invention may be manufactured to be of non-uniform rigidity in order to be adapted to the structural and functional characteristics of a particular valvular graft. Moreover, a polymer material of a resorbable stent of the present invention may be invested with one or more biological response modifiers. The biological response modifiers may include without limitation cell adhesion molecules, growth factors and differentiation factors.

The invention further comprises a method for treating a patient having a defective aortic valve, providing a bioprosthetic heart valve as described above, and surgically implanting the heart valve in the heart of the patient. The invention is applicable to patients requiring implantation of a bioprosthetic heart valve adapted to function at the aortic, mitral, tricuspid or pulmonic valve positions of the heart.

DETAILED DESCRIPTION

Figure 1:
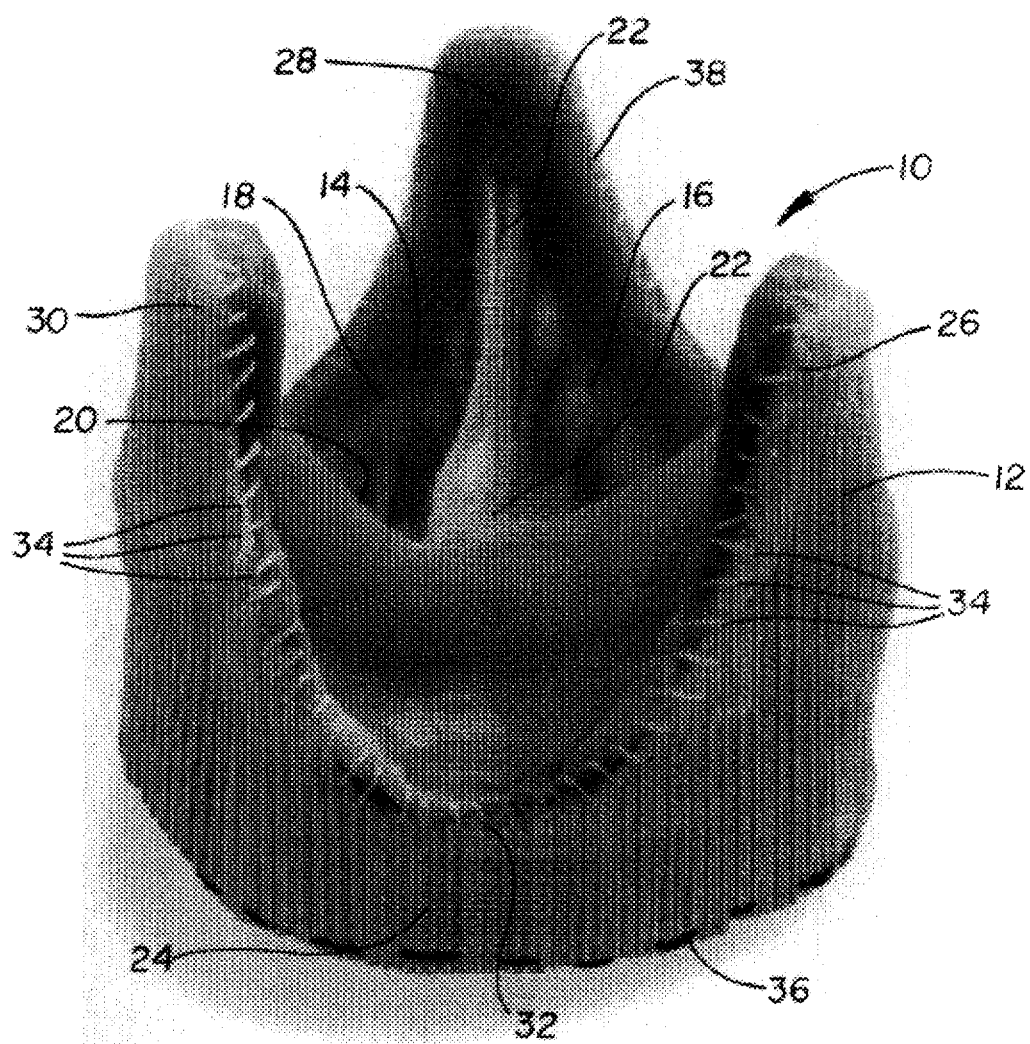
FIG. 1 is a perspective view of a bioprosthetic heart valve comprising a porcine valvular graft and a resorbable sheath-type stent of the present invention.

The resorbable stents for prosthetic heart valves of the present invention create a new class of implantable heart valves, merging the benefits of stented and stentless valves. Using the stent and heart valve of the present invention, the surgeon is able to implant a bioprosthetic valve using a relatively simple procedure, comparable to that used for stented valves. Over time, the stent is resorbed, thereby yielding the hemodynamic benefits now observed with stentless valves. The patients additionally benefit from decreased crossclamp and bypass times during surgery, as well as from the improvement in quality of life that results from improved hemodynamics.

The resorbable stent of the present invention serves to support the bioprosthetic valve and provides for close approximation of the valve and adjacent host structures, allowing for rapid tissue ingrowth and effective tissue remodelling by the host. The resorbable stent provides a mechanical scaffold facilitating implantation with a minimum of suturing at the valve outflow aspect. This provides for relatively natural opening and closing of the valve leaflets without prolapse or perivalvular leakage. Preferably the stent is of the minimum possible thickness permitted by the particular resorbable material used for construction, allowing the largest possible bioprosthetic valve to be used for the implant.

The resorbable stent has mechanical properties sufficient to support the valve during implantation and during the post-implant healing period, while allowing the function of the adjacent structures, for example the aorta, to be retained. Preferably the stent is of sufficient flexibility such that the native compliance of the adjacent host structures (e.g., aorta) and of the valve commissures is not significantly reduced.

Preferably, the bioresorbable material of the stent degrades, post implantation, at a rate that allows good tissue incorporation, but that also results in sufficient resorption within the normal post-operative period, approximately 4–6 months. A variety of resorbable, biocompatible materials, for example polymers, may be employed for manufacture of the stent of the present invention. Homopolymers and copolymers such as those disclosed in U.S. Pat. No. 5,412,068, incorporated herein by reference, are appropriate for the resorbable stents of the present invention. Other polymers include without limitation dextran, hydroxyethyl starch, gelatin, derivatives of gelatin, polyvinylpyrolidone, polyvinyl alcohol, poly[N-(2-hydroxypropyl) methacrylamide], polyglycols, polyesters, poly (orthoesters), poly (ester-amides) and polyanhydrides. Preferably the stents of the present invention are fashioned from polyesters such as poly (hydroxy acids) and copolymers thereof, poly ($\epsilon$-caprolactone), poly (dimethyl glycolic acid), or poly (hydroxy butyrate).

Most preferably the stents are manufactured of polymers of D,L-polylactic acid, L-polylactic acid, or glycolic acid, or copolymers (two or more) of D,L-polylactic acid, L-polylactic acid, and glycolic acid. Such polymers may be manufactured and configured as disclosed, for example, in U.S. Pat. No. 5,133,755, incorporated by reference herein.

It will be apparent to the average skilled artisan that particular bioresorbable materials may be chosen to fit particular patient needs. For example, polymers may be chosen to be resorbed within the normal 4–6-month interval referenced above, but other polymers may be chosen to be resorbed within shorter or longer intervals. Variations in selected times to resorption may depend on, for example, the over-all health of the patient, variations in anticipated immune reactions of the patient to the implant, the site of implantation, and other clinical indicia apparent to the skilled artisan.

Preferably the fabricated resorbable stent has an open, interconnected porosity allowing rapid clot stabilization and subsequent tissue ingrowth. The porous resorbable stent may be fabricated using any of a variety of processes known to those of average skill in the art, including a "replamineform" process, a positive replication process or common textile processes.

The replamineform process involves infiltrating a porous, inorganic structure (typically, calcium carbonate) with wax, dissolving the calcium carbonate, adding the appropriate monomer or mixture of monomers, polymerizing the monomers, and finally increasing the temperature to withdraw the wax. See, for example, Hiratzka et al., Arch. Surgery 114: 698–702 (1979), incorporated herein by reference. This process yields a positive copy of the porous, inorganic structure. Negative copies or casts of the porous inorganic structure may be made by filling the pores with a selected polymer, then dissolving the inorganic matrix (e.g., calcium carbonate) as a final step. What remains following completion of either the positive- or negative-cast steps of the replamineform process is a polymer with defined porosity.

A positive replication process is disclosed in, for example, Jamshidi et al., Resorbable Structured Porous Materials in the Healing Process of Hard Tissue Defects, ASAIO 34:

755–60 (1988), incorporated herein by reference. In principle, a positive replication process is very similar to the replamineform process.

In a further alternative embodiment, porosity can also be introduced by mixing the polymer with particles of a specific size range (e.g., 20 to 300 micron diameters), then dissolving those particles during a final stage of the fabrication process. For example, sodium chloride crystals may be incorporated into a polymer or copolymer by adding crystals of the salt to a solution of dissolved polymer. After evaporating the solvent, annealing the polymer or copolymer by heating, and cooling at controlled rates, the sodium chloride crystals may be leached out using water. This leaves a porous polymer matrix. Porosity and pore size may be controlled by varying the concentration and size of the crystals. See, for example, Hubbell and Langer, Chem. & Engineering News, Mar. 13, 1995, pages 47–50.

The open porosity of the above-described resorbable stents provides a scaffold for cellular ingrowth. To facilitate ingrowth of host or other cells either before or after implantation, a variety of biological response modifiers may be incorporated into the structure of the resorbable stent. Biological response modifier molecules may be covalently or non-covalently coupled to the various internal and external surfaces defining the porosity of the resorbable stent, or may be incorporated directly into the resorbable material during, for example, the polymerization process. In the latter case, the biological response modifier is slowly released as the stent is resorbed.

Appropriate biological response modifiers may include, for example, cell adhesion molecules, cytokines including growth factors, and differentiation factors. Mammalian cells, including those cell types useful or necessary for populating the resorbable stent of the present invention, are anchorage-dependent. That is, such cells require a substrate on which to migrate, proliferate and differentiate.

Cell adhesion molecules (CAM) may be incorporated into the resorbable stent in order to stimulate cell attachment, which is critical for normal cell function. Various CAM useful for incorporation include without limitation fibronectin, vitronectin, fibrinogen, collagen and laminin. See, e.g., Beck et al., J. FASEB 4: 148–160 (1990); Ruoslahti et al., Science 238: 491–97 (1987). The cell attachment activity has been isolated to specific amino acids sequences (expressed herein with standard single-letter code), for example RGD in the case of fibronectin, fibrinogen, collagen, osteopontin and others, REDV from fibronectin and YIGSR from laminin. Hubbell et al., Bio/Technology 9: 586–72 (1991); Humphries et al., J. Cell Biol. 103: 2637–47 (1986); Graf et al., Cell 48: 989–96 (1987). Other examples of cell attachment domains include the heparin-binding domains of fibronectin, KQAGDV and GPRP-containing peptides of fibrinogen and EILDV-containing peptides of fibronectin. Hynes et al., Cell 69: 11–25 (1992); Loike et al., Proc. Natl. Acad. Sci. USA 88: 1044–48 (1991). Thus, any cell attachment peptide-containing molecules functional as CAM for the cells seeded onto or migrating into the resorbable stent may be incorporated into the stent structure during or after fabrication.

The bioresorbable stent may also be fabricated to have a structure conducive to formation of a stabilized blood clot after implantation. These include without limitation stents with relatively high porosity, i.e., relatively high internal surface area. Alternatively, the stabilized clot may be induced to form by inclusion of chemicals, e.g., coagulants, into the stent structure as described above. Inducing a stabilized clot layer to form on the surface upon implantation facilitates cell ingrowth and healing, with the clot layer potentially functioning as a provisional matrix for healing, comparable to that occurring during normal vessel repair. Van Der Lei et al., Int. Angiol. 10: 202–08 (1991), for example, reported on the poor healing of expanded polytetrafluoroethylene prostheses in general, but also reported success in encouraging complete healing by inducing a clot layer to form on the graft surface upon implantation.

Cellular ingrowth may be further facilitated through use of growth factors, including without limitation the fibroblast growth factors including acidic (1), basic (2) and FGF 3 through 9, platelet-derived growth factors including PDGF, PDGF-AA, PDGF-BB and PDGF-AB, transforming growth factors ($\beta1$–$\beta5$), epidermal growth factors including heparin-binding EGF, transforming growth factor $\alpha$ and other members of the epidermal growth factor family, the insulin-like growth factors I and II, platelet-derived endothelial cell growth factor and vascular endothelial growth factor. These factors have been shown to stimulate cellular migration (useful for attracting the appropriate cell population(s) into the stent), proliferation (cell replication) and protein synthesis (required for production of extracellular matrix as the newly indwelling cells remodel the resorbing structure of the stent). Albumin may be added to a particular growth factor to increase its effectiveness. Murray et al., Cancer Drug Delivery 1: 119 (1984).

Other biological response modifiers that may be incorporated into the resorbable stent of the present invention include without limitation polysaccharides, mucopolysaccharides, glycoproteins, and glycosaminoglycans such as hyaluronic acid, chondroitin, chondroitin 4-sulfate, dermatan sulfate, keratan sulfate, heparin, heparan sulfate, alginate, poly-D-lysine, laminin and collagen types I, III and IV. It will be apparent to the average skilled artisan that variations in individual biological response modifiers or combinations of biological response modifiers may be employed to suit the requirements of particular cell types, stent materials, stent configurations, sites of implantation and patient needs.

Referring now to the Figures, a bioprosthetic heart valve with a resorbable stent may be fashioned to have an appearance very similar to the current Toronto SPV® valve (see, e.g., FIG. 1), marketed by St. Jude Medical, Inc., St. Paul, Minn. The Toronto SPV® valve is designed for implantation at the aortic valve position. See, for example, David et al., J. Heart Valve Dis. 1: 244–48 (1992). It will be appreciated by the skilled artisan, however, that the stent of the present invention is applicable to any heart valve that has been adapted or is adaptable to a stented configuration.

Figure 2:
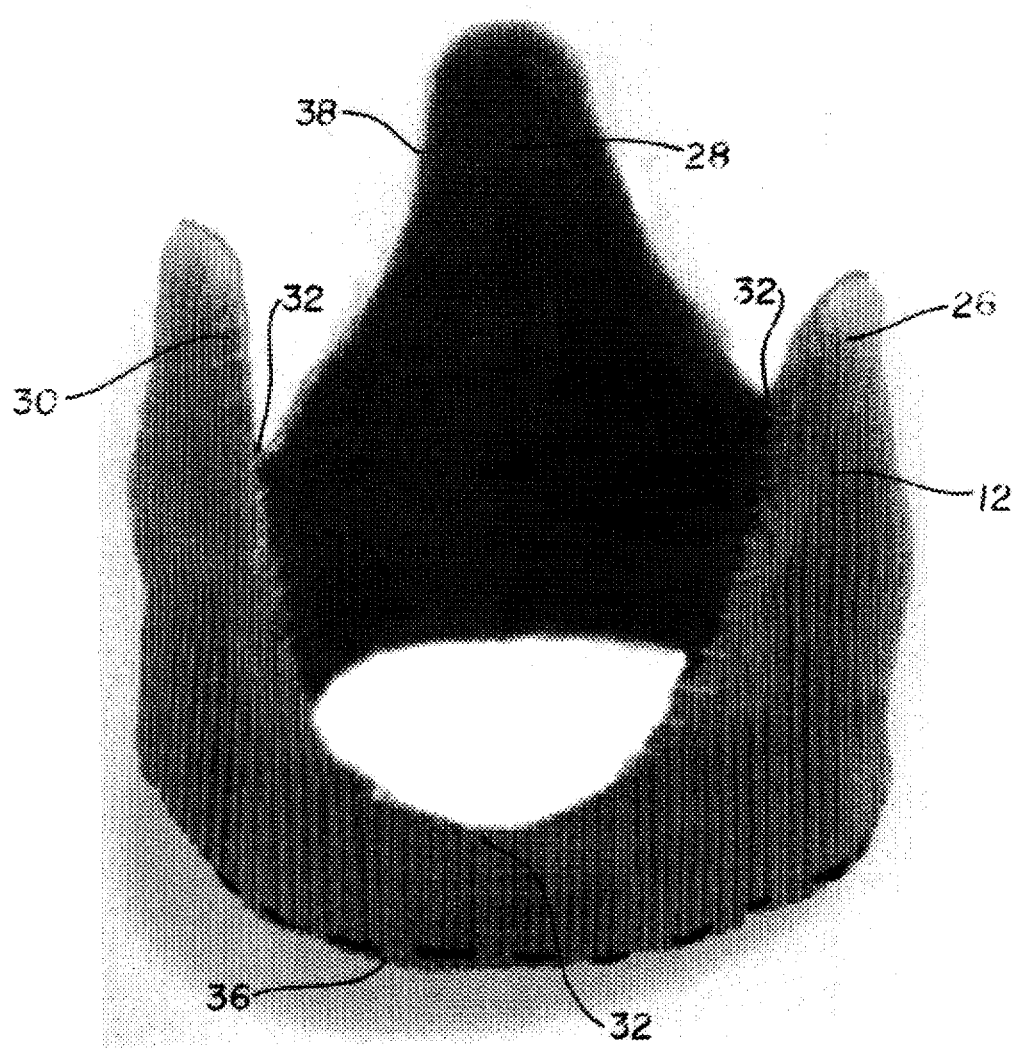
FIG. 2 is a perspective view of a resorbable sheath-type stent of the present invention, viewed in isolation from a valvular graft tissue.

As depicted in FIG. 1 and FIG. 2, the valve 10 comprises a resorbable stent 12 and a valvular graft 14 adapted for implantation in the aortic position. Typically, the graft would constitute a cross-linked porcine xenograft. However, the stent may be used to support grafts from other species and, when appropriate, may provide support for a homograft.

The graft 14 has three leaflets 16, 18 and 20 meeting along commissures 22. The resorbable stent 12 may comprise a sheath contoured to the external surface of the valvular graft, as depicted in FIG. 1. In this configuration, the stent 12 consists of a generally annular base 24 and a triad of axially-projecting and circumferentially-spaced commissure supports 26, 28 and 30 communicating at their spaced lower ends by arcuate connecting portions 32.

The resorbable material of the stent 12 preferably is flexible, allowing inward and outward bending of the commissure supports 26, 28, 30 as well as limited deformability of the base 24. Preferably the flexibility of the stent 12 is selected and manufactured to approximate that of the valvular graft and its native supporting structure. As desired, the rigidity of the stent (reflective of flexibility) may vary from one point to another on the stent, i.e., the stent may be of non-uniform rigidity. For example, the stent may be manufactured of a resorbable polymer such that the base 24 is more or less rigid than the commissure supports 26, 28, 30. Alternatively, rigidity of the resorbable polymeric stent material may vary continuously from one region of the stent 12 to another region, or may vary in multiple step-wise increments from one region to another.

The bioresorbable sheath-type stent 12 is preferably attached to the valvular graft 14 using a continuous suture technique similar to that used to attach a non-resorbable polyester cloth to the current Toronto SPV® valve. Referring to FIG. 1, sutures 34 ate found along the entire inflow 36 and outflow 38 edges of the valve 10 to ensure adequate attachment of the stent 12 to the valvular graft 14. Other techniques, including non-suturing techniques, are adaptable to attachment of the sheath-type stent to the valvular graft. These include, without limitation, laser-induced welding of the resorbable stent to the valvular graft.

Figure 3:
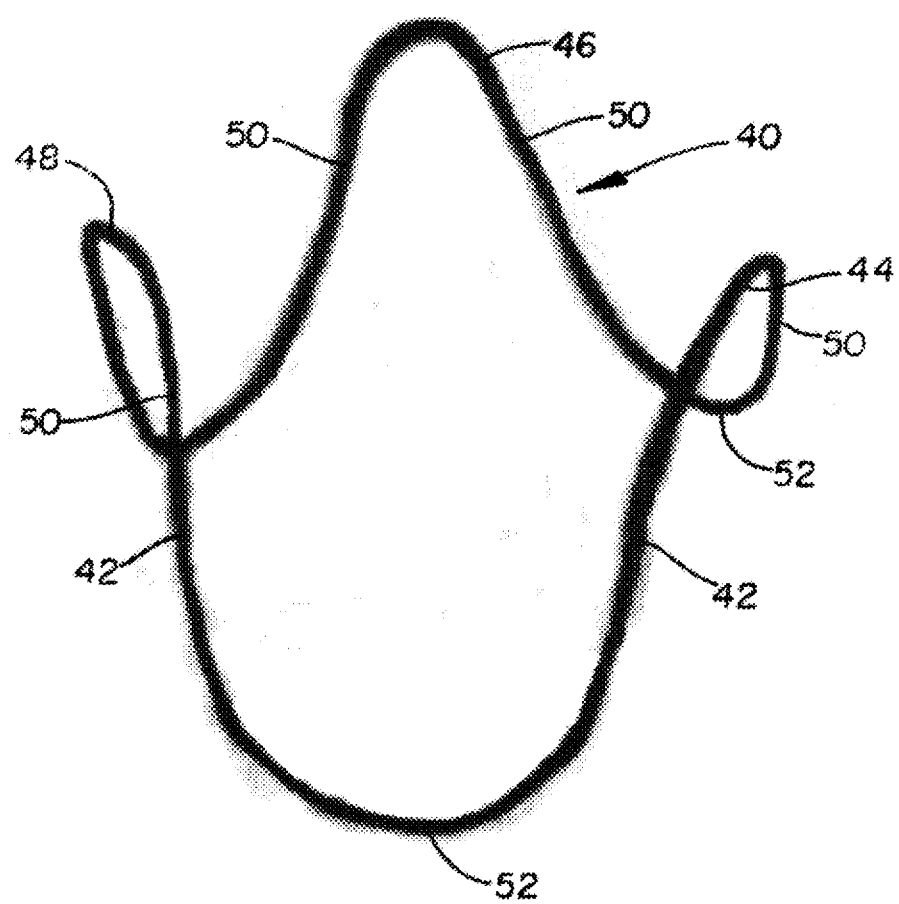
FIG. 3 depicts a frame-type stent of the present invention.

In an alternative embodiment depicted in FIG. 3, the invention comprises a frame-type stent 40. The frame is contoured to conform to the shape of a valvular graft. In the embodiment depicted in FIG. 3, the frame is adapted to be used with a valve similar in configuration to the current Toronto SPV® valve. It will be appreciated by the skilled artisan, however, that the frame-type stent 40 may have a wide range of shapes to conform to any selected valvular graft configuration.

As depicted in FIG. 3, the stent 40 comprises an elongated flexible frame member 42 of over-all generally annular configuration. The frame member 42 may be generally circular in cross section, or may be oval or flattened in cross section. The frame member 42 is formed to define a triad of axially-projecting and circumferentially-spaced commissure supports 44, 46 and 48. As shown in FIG. 3, each commissure support is of generally U-shaped configuration, having legs 50 bending smoothly at their spaced lower ends with arcuate connecting portions 52.

The resorbable material of the frame member 42 preferably is flexible, allowing inward and outward bending of the commissure supports 44, 46, 48 as well as limited deformability of the frame-type stent 40 as a whole. Preferably the flexibility of the frame member 42 is selected and manufactured to approximate that of the valvular graft and its native supporting structure. As desired, the rigidity of the frame-type stent 40 (reflective of flexibility) may vary from one point to another on the stent, i.e., the stent 40 may be of non-uniform rigidity. For example, the stent may be manufactured of a resorbable polymer such that the arcuate connecting portions 52 are more or less rigid than the legs 50. Alternatively, rigidity of the resorbable polymeric stent material may vary continuously from one region of the stent 40 to another region, or may vary in multiple step-wise increments from one region to another.

The bioresorbable frame-type stent is preferably attached to the valvular graft using a winding suture around the frame, with the suture passing through the tissue of the valvular graft with each wind. As with the sheath-type resorbable stent, the frame-type stent may be attached to the valvular graft with other procedures, including without limitation laser-induced welding.

In the cases of both the sheath-type and frame-type stents of the present invention, any sutures used for attachment to a valvular graft and to the patient may be bioresorbable. Preferably the resorption rate of the sutures is similar to that of the stent.

A bioprosthetic heart valve with a resorbable stent of the present invention is implantable with a variety of surgical techniques appropriate to the configuration of the valvular tissue and stent and to the site of implantation. These surgical procedures will be apparent to the skilled artisan, and may include without limitation subcoronary implantation techniques similar to those used for free-hand homograft valve implant techniques. Such techniques are disclosed in, for example, R. A. Hopkins, *Cardiac Reconstructions with Allograft Valves*, Springer-Verlag (1989), pages 97–122. Generally, a series of interrupted sutures is placed around the tissue annulus. The valve is then parachuted down the sutures and tied in place. Following this, stay sutures are placed at the commissures to stabilize them into the adjacent host tissue, e.g., the aortic wall. The cardiovascular incision (e.g., aortotomy) is then closed and the heart restarted.

With the bioprosthetic heart valve and resorbable stent of the present invention, cross-clamp times for implantation will approximate those required with present stented valves, in which the stent consists of non-resorbable materials. This opens the "stentless" valve procedures to less skilled surgeons, who may not otherwise have the technical expertise to handle a typical stentless valve's more demanding surgical technique. Thus, additional patients receive the hemodynamic benefit of a "stentless" valve implant.

The foregoing detailed description has been provided for a better understanding of the invention only and no unnecessary limitation should be understood therefrom as some modifications will be apparent to those skilled in the art without deviating from the spirit and scope of the appended claims.

What is claimed is:

1. A bioprosthetic heart valve comprising a valvular tissue graft secured to a biocompatible, is contoured to said valvular tissue graft, said bioprosthetic heart valve being appropriate for joining with valve-receiving cardiac tissue, wherein said stent is operably resorbed following substantially complete healing of said heart valve with said valve-receiving cardiac tissue.

2. The bioprosthetic heart valve of claim 1, wherein said valvular tissue graft is adapted to function at an aortic valve position.

3. The bioprosthetic heart valve of claim 1, wherein said valvular tissue graft is adapted to perform at a mitral valve position.

4. The bioprosthetic heart valve of claim 1, wherein said valvular tissue graft is adapted to perform at a tricuspid valve position.

5. The bioprosthetic heart valve of claim 1, wherein said valvular tissue graft is adapted to perform at a pulmonic valve position.

6. The bioprosthetic heart valve of claim 1, wherein said sheath comprises a biocompatible, resorbable polymer.

7. The bioprosthetic heart valve of claim 6, wherein said polymer is selected from the group consisting of dextran, hydroxyethyl starch, gelatin, derivatives of gelatin, polyvinylpyrolidone, polyvinyl alcohol, poly[N-(2-hydroxypropyl)methacrylamide], polyglycols, polyesters, poly (orthoesters), poly (ester-amides) and polyanhydrides.

8. The bioprosthetic heart valve of claim 7, wherein said polyesters are selected from the group consisting of poly (hydroxy acids) and copolymers thereof, poly ([epsilon]-caprolactone), poly (dimethyl glycolic acid) and poly (hydroxy butyrate).

9. The bioprosthetic heart valve of claim 6, wherein said polymer is selected from the group consisting of D,L-polylactic acid, L-polylactic acid, glycolic acid and copolymers of D,L-polylactic acid, L-polylactic acid, and glycolic acid.

10. The bioprosthetic heart valve of claim 6, wherein said sheath is of non-uniform rigidity.

11. The bioprosthetic heart valve of claim 6, wherein said polymer is invested with one or more biological response modifiers.

12. The bioprosthetic heart valve of claim 11, wherein said one or more biological response modifiers are selected from the group consisting of cell adhesion molecules, growth factors and differentiation factors.

* * * * *

UNITED STATES PATENT AND TRADEMARK OFFICE
CERTIFICATE OF CORRECTION

PATENT NO. : 5,728,152
DATED : March 17, 1998
INVENTOR(S) : M. William Mirsch II, et al.

It is certified that error appears in the above-indentified patent and that said Letters Patent is hereby corrected as shown below:

Column 8, line 40, before "is", insert
--resorbable heart valve stent, said stent comprising a sheath that--

Signed and Sealed this

Fifth Day of January, 1999

Attest:

Attesting Officer

*Acting Commissioner of Patents and Trademarks*